United States Patent [19]
Heath et al.

[11] Patent Number: 5,743,734
[45] Date of Patent: Apr. 28, 1998

[54] PORTABLE HOLDER FOR SAFELY SUPPORTING AND HANDLING SHARP DENTAL INSTRUMENTS

[75] Inventors: Derek E. Heath; Jerry A. Mooneyhan, both of Johnson City; Van T. Himel, Germantown, all of Tenn.

[73] Assignee: Tulsa Dental Products, L.L.C., Tulsa, Okla.

[21] Appl. No.: 655,690

[22] Filed: Jun. 3, 1996

[51] Int. Cl.⁶ .................................................. A61G 15/00
[52] U.S. Cl. ................................................. 433/77; 206/369
[58] Field of Search ........................... 433/77; 206/368, 206/369

[56] References Cited

U.S. PATENT DOCUMENTS

| | | | |
|---|---|---|---|
| 2,983,519 | 5/1961 | Staunt | 433/127 |
| 3,270,416 | 9/1966 | Massa | 433/77 |
| 3,451,133 | 6/1969 | Hathaway et al. | 433/77 |
| 4,253,830 | 3/1981 | Kazen et al. | 433/77 |
| 4,327,060 | 4/1982 | Nisii | 422/300 |
| 4,503,972 | 3/1985 | Nelligan et al. | 206/379 |
| 4,867,305 | 9/1989 | Schneider | 206/368 |
| 5,006,066 | 4/1991 | Rouse | 433/77 |
| 5,071,346 | 12/1991 | Domaas | 433/77 |
| 5,108,287 | 4/1992 | Yee et al. | 433/77 |
| 5,172,810 | 12/1992 | Brewer | 433/77 |
| 5,312,250 | 5/1994 | Ellman et al. | 433/77 |
| 5,358,112 | 10/1994 | Gardner | 206/369 |
| 5,380,200 | 1/1995 | Heath | 433/102 |
| 5,435,979 | 7/1995 | Miller et al. | 433/77 |

*Primary Examiner*—John J. Wilson
*Attorney, Agent, or Firm*—Bell Seltzer Intellectual Property Law Group of Alston & Bird LLP

[57] ABSTRACT

A portable holder for safely supporting a plurality of sharp dental instruments, and which comprises a body member which includes a base plate having a plurality of openings therein for supportingly receiving the instruments. A pressure plate is slideably mounted to the body member immediately below the base plate, and the pressure plate includes a plurality of openings which are aligned with the openings of the base plate and are adapted to receive the shanks of the instruments which are supported in the openings of the base plate. The pressure plate is mounted for slidable movement between a loading position wherein the openings of the base plate and the pressure plate are aligned, and an instrument retaining position wherein the openings are offset so that the instruments are engaged and lock in the openings. The holder facilitates the loading and unloading of the instruments from a dental handpiece, without requiring the dentist or attendant to touch the instruments, and it also facilitates the sterilization of the instruments in an autoclave.

14 Claims, 2 Drawing Sheets

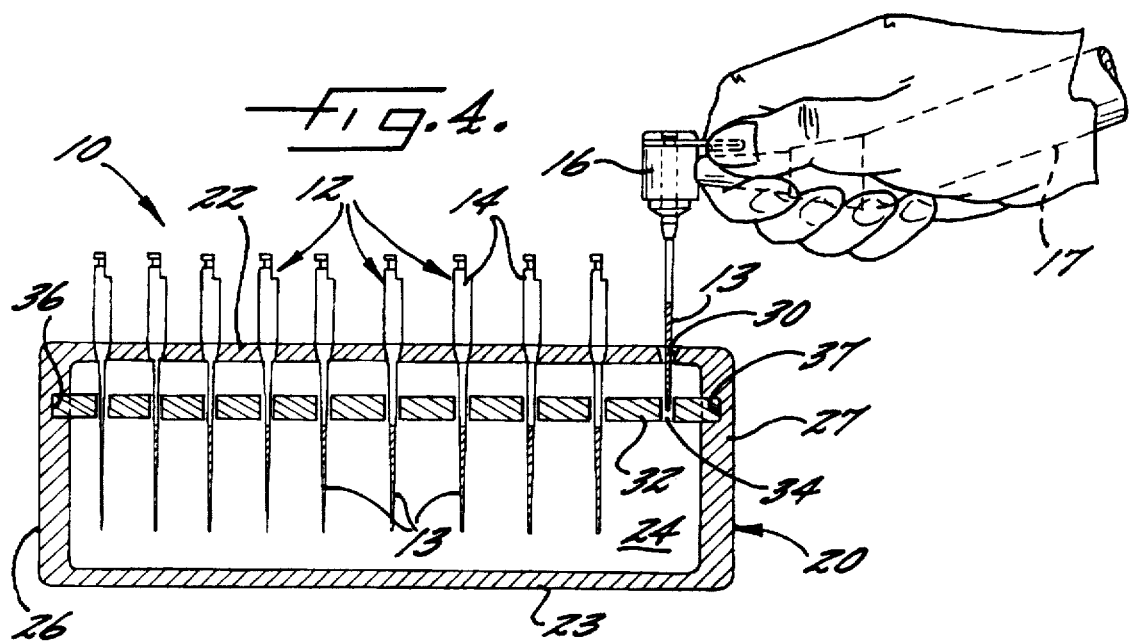
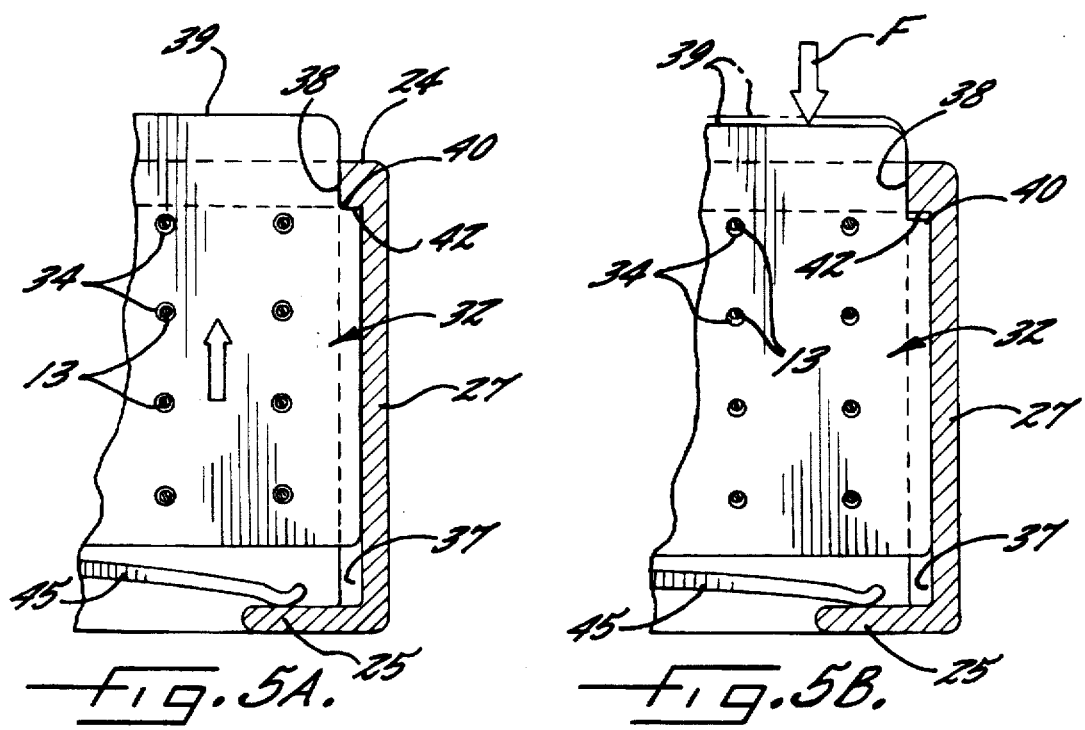
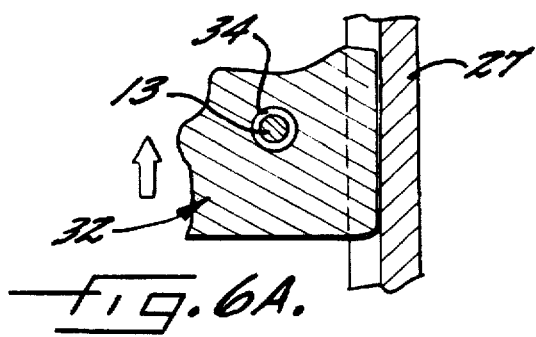
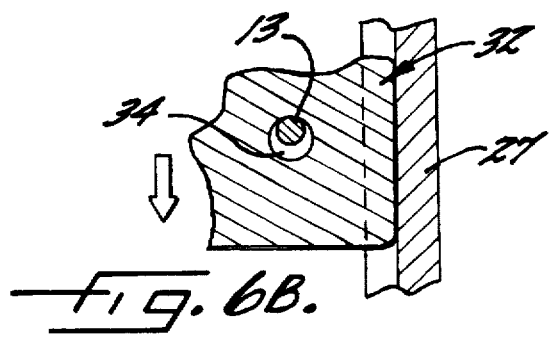

1

PORTABLE HOLDER FOR SAFELY SUPPORTING AND HANDLING SHARP DENTAL INSTRUMENTS

BACKGROUND OF THE INVENTION

The present invention relates to a portable holder for safely supporting and handling sharp instruments used in medical procedures.

In a large number of dental and other medical procedures, a number of sharp needle-like instruments are employed, and the use and handling of such instruments present a danger that one of the instruments could inadvertently engage and pierce the patient or attending medical personnel, causing physical injury and possibly also the transfer of infectious disease.

An endodontic root canal therapy procedure, wherein the crown of a diseased tooth is opened so as to permit the canal to be cleaned and then filled, is one example of a dental procedure wherein a number of such instruments are handled and used. More particularly, during a root canal procedure, a series of very delicate, flexible, needle-like instruments, commonly referred to as files, are used to extirpate or clean out and shape the root canal, and each file is either manually rotated or rotated by a handpiece at a relatively high speed. Files of increasingly larger diameter are used in sequence, to achieve the desired cleaning and shaping. When the canal is thus prepared, it is obturated or solidly filled with a filling material, which typically comprises a waxy, rubbery compound known as gutta percha.

Where a root canal procedure is practiced using instruments which are sequentially mounted to a handpiece, the instruments include an enlarged head which is releasably engaged by the chuck of the handpiece. More particularly, the head of each instrument includes a notch which mates with a corresponding notch in the chuck of the handpiece, and to properly seat the instrument in the chuck, the instrument must be manually rotated until the notches are aligned. It is also sometimes difficult to remove the instrument, since the instrument can become stuck. The instrument can easily slip in the hand of the dental assistant during these rather difficult manipulations, and there is a danger that the hand of the assistant could be pierced by the instrument.

Another risk associated with the above described procedure is the fact that the latch on the handpiece can be inadvertently released, which allows the instrument to freely fall and possibly pierce the patient or the dentist or one of the attendants.

Handpieces are also available which are designed to engage dental instruments by means of a friction grip chuck, which minimizes the risk of an inadvertent release of an instrument. However, this type of handpiece is not commonly used in endodontic procedures, since the removal of the instruments from a friction grip chuck usually requires the use of a wrench, or a release pin, to open or release the chuck, and the use of these extra components is cumbersome and time consuming particularly in view of the large number of changes of instruments which are typically required in an endodontic procedure. Also, a physical force may occasionally need to be exerted on the instrument by the dentist or the attendant in order to insert it into the chuck or to withdraw it from the chuck. As in the case of the latch type handpiece as described above, this physical handling of the instrument increases the risk that an instrument will inadvertently injure the dentist or attendant.

Another risk associated with the above described procedure occurs during the sterilization of the instruments between procedures. At present, the instruments are normally placed in an autoclave, where they are heated to a sterilizing temperature. Manual handling of the instruments is often required during the procedure, which also increases the risk of injury to the dentist or an attendant.

It is accordingly an object of the present invention to provide a holder for sharp instruments of the described type which permits the instruments to be supported and handled in a manner which avoids human contact with the instruments and thereby reduces the risk of inadvertent injury to the patient or the dental personnel.

It is another object of the present invention to provide a holder for sharp medical instruments which is able to safely support the instruments during an autoclaving procedure.

It is another more particular object of the present invention to provide a holder for sharp dental instruments which permits the instruments to be unloaded from and loaded into the chuck of a dental handpiece, without requiring that the instruments be directly touched by the dental personnel.

SUMMARY OF THE INVENTION

The above and other objects and advantages of the present invention are achieved by the provision of a holder which comprises a body member which includes a base plate having a plurality of openings therein. The openings which are sized to permit the shank of an instrument to pass therethrough while engaging the head, so as to permit a plurality of the instruments to be supportingly received in the openings of the base plate. A pressure plate is provided which has a plurality of openings therein which are sized to permit the shank of an instrument to pass therethrough and which are arranged in a pattern matching that of the openings in the base plate. The pressure plate is slidably mounted to the body member so that the pressure plate is parallel to and below the base plate and so as to be slidable between a loading position wherein the openings of the base plate and the pressure plate are respectively aligned, and an instrument retaining position wherein the openings are respectively offset. A biasing member is also provided for biasing the pressure plate toward one of the loading position and the retaining position and such that the pressure plate is normally retained in said one of the positions and may be moved to the other of the positions by manually pressing the pressure plate in a direction against the force of said biasing means. Preferably, the biasing member acts to bias the pressure plate toward the open position.

In the preferred embodiment, the body member defines a hollow parallelepiped which is defined by the base plate, a bottom wall opposite the base plate, front and rear walls, and opposite side walls. Also, the mounting means for the pressure plate includes a pair of opposing slots in respective ones of the opposite side walls which extend in a direction parallel to the base plate and which slideably receive the pressure plate therebetween. Further, the front wall includes an elongate opening which is aligned with the pressure plate, and the pressure plate is sized so as to define a front edge portion which extends through the opening and is manually accessible on the outside of the body member.

In use, a plurality of instruments may be positioned in the pairs of aligned openings in the base plate and the pressure plate, and while the pressure plate is in the loading position. The handpiece may then be moved onto the head of a selected instrument, so as to couple the handpiece to the instrument, and the instrument may then be withdrawn with the handpiece so as to permit it to be used in the normal manner. When its use is completed, the shank of the instrument can then be returned to a pair of aligned openings, and upon manually pressing the pressure plate, the shank is securely held and the handpiece may be lifted away and separated from the instrument. These operations can be repeated with several differently sized instruments, without need for the dentist or the dental assistant to ever touch the instruments. The risk of injury is thereby minimized.

BRIEF DESCRIPTION OF THE DRAWINGS

Some of the objects and advantages of the present invention having been stated, others will appear as the description proceeds, when considered in conjunction with the accompanying drawings, in which:

FIG. 4 is a sectional side view of the holder taken substantially along the line 4—4 of FIG. 2;

FIGS. 5A and 5B are enlarged fragmentary views corresponding to FIG. 2, and illustrating the pressure plate in its loading position and instrument retaining position, respectively;

FIGS. 6A and 6B are enlarged fragmentary views illustrating one of the openings of the pressure plate and the associated instrument, of FIGS. 5A and 5B, respectively.

DETAILED DESCRIPTION OF THE PREFERRED EMBODIMENT

Figure 1:
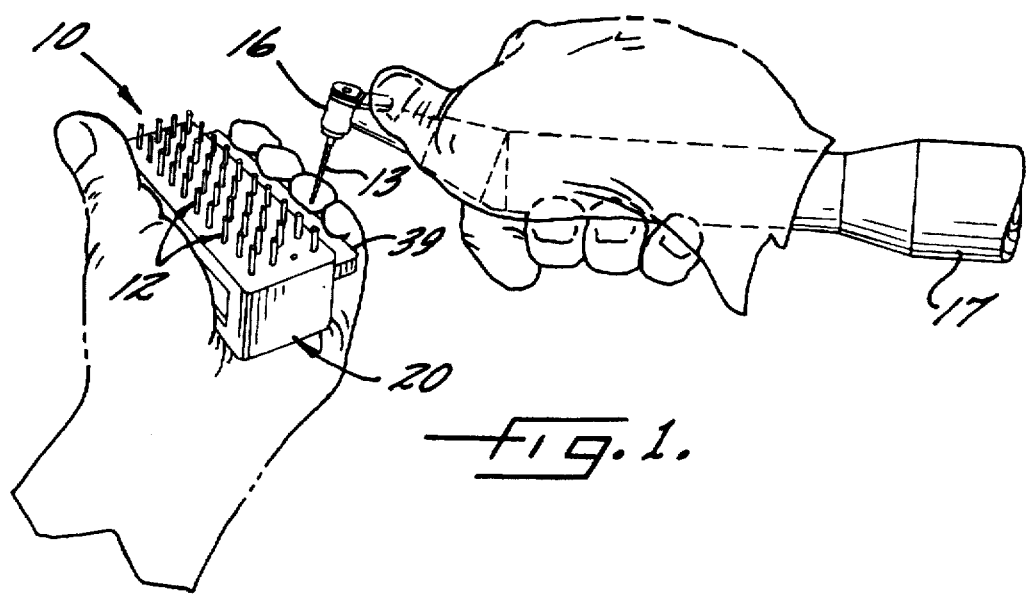
FIG. 1 is a perspective view of an instrument holder which embodies the features of the present invention, and which illustrates its manner of use.

Referring more particularly to the drawings, a portable holder which embodies the features of the present invention is indicated generally at 10. As will become apparent, the holder 10 is adapted for supporting a plurality of endodontic instruments 12 of the type comprising an elongate shank 13 and an enlarged head 14 at one end of the shank which is adapted to be engaged and rotated by the chuck 16 a dental handpiece 17. A further description of an endodontic instrument of the described type may be obtained from U.S. Pat. Nos. 4,934,934 and 5,464,362, the disclosures of which are expressly incorporated herein by reference. Also, a handpiece of the described type is conventional and is further illustrated in U.S. Pat. No. 2,983,519, the disclosure of which is also incorporated herein by reference.

The holder 10 comprises a box like body member 20 which defines a hollow parallelepiped, which comprises a top wall 22 (herein referred to as a base plate), a bottom wall 23, front and rear walls 24, 25 and opposite side walls 26, 27. The body member 20 may be fabricated or molded from any suitable metal, plastic, or glass material which is able to withstand normal autoclaving temperatures, and it is preferably sized to permit it to be easily grasp and held in one hand of the user as seen in FIG. 1.

The base plate 22 of the holder 20 includes a plurality of openings 30 which are arranged in a rectangular pattern as illustrated, and which are sized to permit the shank 13 of an instrument to pass therethrough while engaging the head 14, so as to permit a plurality of instruments 12 to be supportingly received in the openings 30 of the base plate, as best seen in FIGS. 1 and 4.

The holder 10 also includes a pressure plate 32 which has a plurality of openings 34 therein which are sized to permit the shank 13 of an instrument 12 to pass therethrough and which are arranged in a rectangular pattern matching that of the openings 30 of the base plate 22. The pressure plate 32 is slideably mounted inside the body member 20 so that the pressure plate 32 is parallel to and below the base plate 22, and so as to be slidable between a loading position (FIGS. 5A, 6A) wherein the openings 30 of the base plate 22 and the openings 34 of the pressure plate 32 are respectively aligned, and an instrument retaining position (FIGS. 5B, 6B) wherein the openings 30, 34 of the base plate and the pressure plate are respectively offset so as to lock the shank 13 of the instrument 12 in its retained position.

The pressure plate 32 is mounted within the body member 20 by means of a pair of opposing slots 36, 37 in the opposite side walls 26, 27, which extend in a direction parallel to the base plate 22 and which slideably receive opposite edges of the pressure plate 32 therein. Further, the front wall 24 of the body member includes an elongate opening 38 which is aligned with the pressure plate 32, and the pressure plate is sized so as to define a front edge portion 39 which extends through the opening 38 so as to be manually accessible on the outside of the body member 20 as best seen in FIG. 1.

The opposite ends of the front edge portion 39 of the pressure plate include a forwardly facing shoulder 40 which is positioned to engage a mating lip 42 formed by the front wall 24 at the end of the elongate opening 38, and so as to define the loading position. In addition, a biasing member is provided for biasing the pressure plate 32 toward the loading position and such that the pressure plate is normally retained in the loading position with the shoulder 40 in engagement with the lip 42. As will become apparent, the pressure plate 32 may be moved rearwardly from the loading position to the instrument retaining position as shown in FIGS. 5B and 6B, by manually pressing the pressure plate in the direction of the arrow F.

In the illustrated embodiment, the biasing member comprises a pair of oppositely directed tabs 44, 45 which are integrally attached to the rear side of the pressure plate 32, and so as to resiliently engage the rear wall 25.

Figure 2:
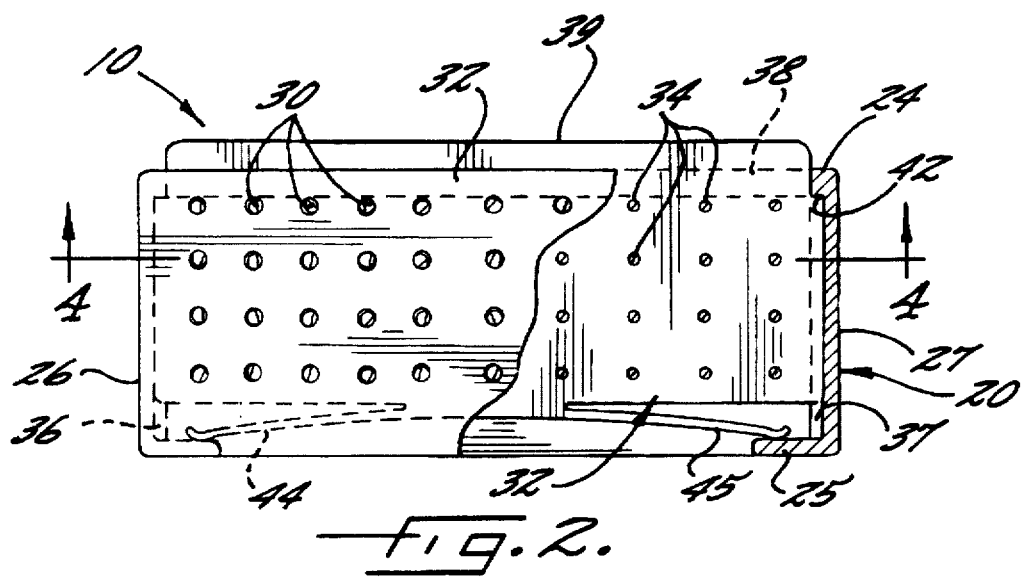
FIG. 2 is a top plan view of the holder shown in FIG. 1, partly broken away to illustrate the interior thereof.
Figure 3:
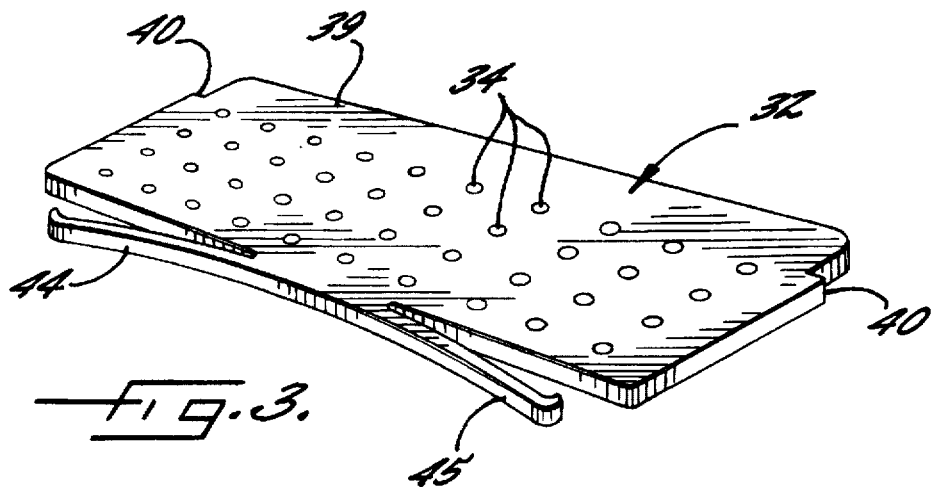
FIG. 3 is a perspective view of the pressure plate used in the holder of the present invention.

As best seen in FIGS. 1 and 2, the rear wall 25 is essentially open, and it comprises only a peripheral edge. This permits the interior of the body member 20 to be readily cleaned, and it also facilitates sterilization of the body member and the instruments during an autoclaving operation. If desired, others of the walls of the body member 20 may be partially or completely opened, for these purposes.

As indicated above, endodontic instruments of the described type are commonly provided in a range of sizes (or diameters) which are used sequentially in a root canal procedure. To facilitate the identification and use of the instruments, the openings 30 may be of slightly different diameters and labels (not shown) may be provided on the upper surface of the base plate 22 to indicate the size of the instrument intended to be received in each opening 30.

To now describe the operation and use of the holder 10 during for example an endodontic procedure, it will be assumed that the holder is initially loaded with a plurality of instruments 12 or files of different sizes as shown in FIGS. 1 and 4. The handpiece 17 is then brought to the holder, and the chuck 16 of the handpiece 17 is positioned to receive the head 14 of one of the instruments 12 in the conventional manner. The pressure plate 32 at this time is positioned in its loading position as seen in FIGS. 5A and 6A, by reason of the force provided by the tabs 44, 45 which bias the pressure plate so that the shoulders 40 engage the lips 42.

The handpiece 17 and the retained instrument 12 are then withdrawn and used by the dentist in the conventional manner, and when it is desired to change the size of the instrument, the handpiece is brought back to the holder 10 and the original instrument is deposited in a pair of aligned openings of proper size in the base plate 22 and pressure plate 32. To facilitate the release of the instrument from the handpiece 17, the attendant manually squeezes the pressure plate 32 rearwardly in the direction of force F so that the pressure plate is moved to its instrument retaining position as seen in FIGS. 5B and 6B, causing the pair of openings retaining each instrument to be offset and thereby lock the instruments therein. The handpiece 17 can then be withdrawn from the instrument 12, without the attendant ever touching the instrument. These operations are repeated as necessary, and upon completion of the endodontic procedure, the holder 10 and all of the instruments may be readily deposited in an autoclave to effect the sterilization of the instruments.

In the drawings and the specification, there has been set forth a preferred embodiment of the invention and, although specific terms are employed, the terms are used in a generic and descriptive sense only and not for the purpose of limitation, the scope of the invention being set forth in the following claims.

That which is claimed is:

1. A portable holder for supporting dental instruments of the type comprising an elongate shank and an enlarged head at one end of the shank, and comprising a body member including a base plate having a plurality of openings therein which are each sized to permit the shank of an instrument to pass therethrough while engaging the head so as to permit a plurality of the instruments to be supportingly received in the openings of the base plate, a pressure plate having a plurality of openings therein which are sized to permit the shank of an instrument to pass therethrough and which are arranged in a pattern matching that of the openings in the base plate, means slideably mounting the pressure plate to the body member so that the pressure plate is parallel to and below the base plate and so as to be slidable between a loading position wherein the openings of the base plate and the pressure plate are respectively aligned, and an instrument retaining position wherein the openings are respectively offset, and means biasing the pressure plate toward one of the loading position and the retaining position and such that the pressure plate is normally retained in said one of the positions and may be moved to the other of said positions by manually pressing the pressure plate in a direction against the force of said biasing means.

2. The portable holder as defined in claim 1 wherein said biasing means acts to bias said pressure plate toward said open position.

3. The portable holder as defined in claim 1 wherein said body member defines a hollow parallelepiped which is defined by said base plate, opposite front and rear walls, and opposite side walls.

4. The portable holder as defined in claim 3 wherein said mounting means includes a pair of opposing slots in respective ones of said opposite side walls which extend in a direction parallel to said base plate and which slideably receive said pressure plate therebetween.

5. The portable holder as defined in claim 4 wherein said front wall includes an elongate opening which is aligned with said pressure plate, and wherein said pressure plate is sized so as to define a front edge portion which extends through said opening and is manually accessible.

6. The portable holder as defined in claim 5 wherein said front wall and said pressure plate include interengaging shoulder means which define said one position.

7. The portable holder as defined in claim 6 wherein said biasing means comprises spring means interposed between said pressure plate and said rear wall of said body member.

8. The portable holder as defined in claim 7 wherein said spring means includes a tab integrally attached to said pressure plate and positioned to extend into engagement with said rear wall.

9. The portable holder as defined in claim 6 wherein said body member further comprises a bottom wall which is opposite said base wall, and wherein at least one of said front and rear walls and said bottom wall includes a relatively large opening therein so as to permit the interior of the body member to be readily cleaned and sterilized.

10. A portable holder for supporting dental instruments of the type comprising an elongate shank and an enlarged head at one end of the shank, and comprising a body member which defines a hollow parallelepiped which includes a base plate, opposite front and rear walls, and opposite side walls, said base plate having a plurality of openings therein which are each sized to permit the shank of an instrument to pass therethrough while engaging the head so as to permit a plurality of the instruments to be supportingly received in the openings of the base plate, a pressure plate having a plurality of openings therein which are sized to permit the shank of an instrument to pass therethrough and which are arranged in a pattern matching that of the openings in the base plate, means slideably mounting the pressure plate to the body member so that the pressure plate is parallel to and below the base plate and so as to be slidable between a loading position wherein the openings of the base plate and the pressure plate are respectively aligned, and an instrument retaining position wherein the openings are respectively offset, said mounting means including a pair of opposing slots in respective ones of said opposite side walls which extend in a direction parallel to said base plate and which slideably receive said pressure plate therebetween, and means biasing the pressure plate toward said loading position and such that the pressure plate is normally retained in said loading positions and may be moved to the other of said positions by manually pressing the pressure plate in a direction against the force of said biasing means.

11. The portable holder as defined in claim 10 wherein said front wall includes an elongate opening which is aligned with said pressure plate, and wherein said pressure plate is sized so as to define a front edge portion which extends through said opening and is manually accessible.

12. The portable holder as defined in claim 11 wherein said front wall and said pressure plate include interengaging shoulder means which define said loading position.

13. The portable holder as defined in claim 12 wherein said biasing means comprises spring means interposed between said pressure plate and said rear wall of said body member.

14. The portable holder as defined in claim 13 wherein said openings in said base plate are not of uniform diameters so as to accommodate instruments of different types.

* * * * *